(12) United States Patent
Chin et al.

(10) Patent No.: US 8,486,099 B2
(45) Date of Patent: Jul. 16, 2013

(54) SYSTEMS AND METHODS FOR REMOVAL OF INTRAVASCULAR LEADS

(75) Inventors: Albert K. Chin, Palo Alto, CA (US); Lishan Aklog, Scottsdale, AZ (US)

(73) Assignee: Pavilion Medical Innovations, LLC, Norwell, MA (US)

( * ) Notice: Subject to any disclaimer, the term of this patent is extended or adjusted under 35 U.S.C. 154(b) by 231 days.

(21) Appl. No.: 13/010,680

(22) Filed: Jan. 20, 2011

(65) Prior Publication Data
US 2011/0178543 A1   Jul. 21, 2011

Related U.S. Application Data

(60) Provisional application No. 61/296,610, filed on Jan. 20, 2010, provisional application No. 61/305,824, filed on Feb. 18, 2010, provisional application No. 61/314,883, filed on Mar. 17, 2010, provisional application No. 61/332,007, filed on May 6, 2010, provisional application No. 61/362,070, filed on Jul. 7, 2010, provisional application No. 61/368,898, filed on Jul. 29, 2010, provisional application No. 61/420,008, filed on Dec. 6, 2010.

(51) Int. Cl.
    *A61B 17/00*   (2006.01)
(52) U.S. Cl.
    USPC ........................................... 606/190; 604/22
(58) Field of Classification Search
    USPC ................ 606/108, 159, 170, 190; 604/22
    See application file for complete search history.

(56) References Cited

U.S. PATENT DOCUMENTS

| 4,046,149 | A | * | 9/1977 | Komiya ..................... 606/127 |
| 4,471,777 | A | | 9/1984 | McCorkle, Jr. |
| 4,582,056 | A | | 4/1986 | McCorkle, Jr. |
| 5,441,510 | A | | 8/1995 | Simpson et al. |
| 5,651,781 | A | | 7/1997 | Grace |
| 5,680,860 | A | | 10/1997 | Imran |
| 5,785,715 | A | | 7/1998 | Schatz |
| 5,947,983 | A | | 9/1999 | Solar et al. |
| 5,954,720 | A | * | 9/1999 | Wilson et al. ................. 606/50 |
| 6,060,695 | A | | 5/2000 | Harle et al. |
| 6,183,469 | B1 | | 2/2001 | Thapliyal et al. |
| 6,379,351 | B1 | | 4/2002 | Thapliyal et al. |
| 6,419,674 | B1 | | 7/2002 | Bowser et al. |
| 7,344,546 | B2 | | 3/2008 | Wulfman et al. |
| 2008/0154296 | A1 | | 6/2008 | Taylor et al. |
| 2008/0275403 | A1 | | 11/2008 | Maaskamp et al. |
| 2009/0264831 | A1 | | 10/2009 | Thompson et al. |

OTHER PUBLICATIONS

International Search Report based on PCT/US2011/021935 mailed Mar. 23, 2011.
International Search Report based on PCT/US2011/021895 mailed Mar. 25, 2011.
Office Action for U.S. Appl. No. 13/010,447 mailed on Feb. 27, 2013.

* cited by examiner

*Primary Examiner* — Victor Nguyen
(74) *Attorney, Agent, or Firm* — Chinh H. Pham; Roman Fayerberg; Greenberg Traurig, LLP

(57) ABSTRACT

Systems and methods for extraction of implanted articles are disclosed. According to aspects illustrated herein, there is provided a system for extraction of an implanted article that includes an elongated member and a guide member disposed at a distal section of the elongated member. The guide member may define a pathway through which an implanted article can be securely received. The device can further include a dissection mechanism, coupled to the elongated member and designed to be positioned about the implanted article, for dissecting a fibrous adhesion about the implanted article.

14 Claims, 15 Drawing Sheets

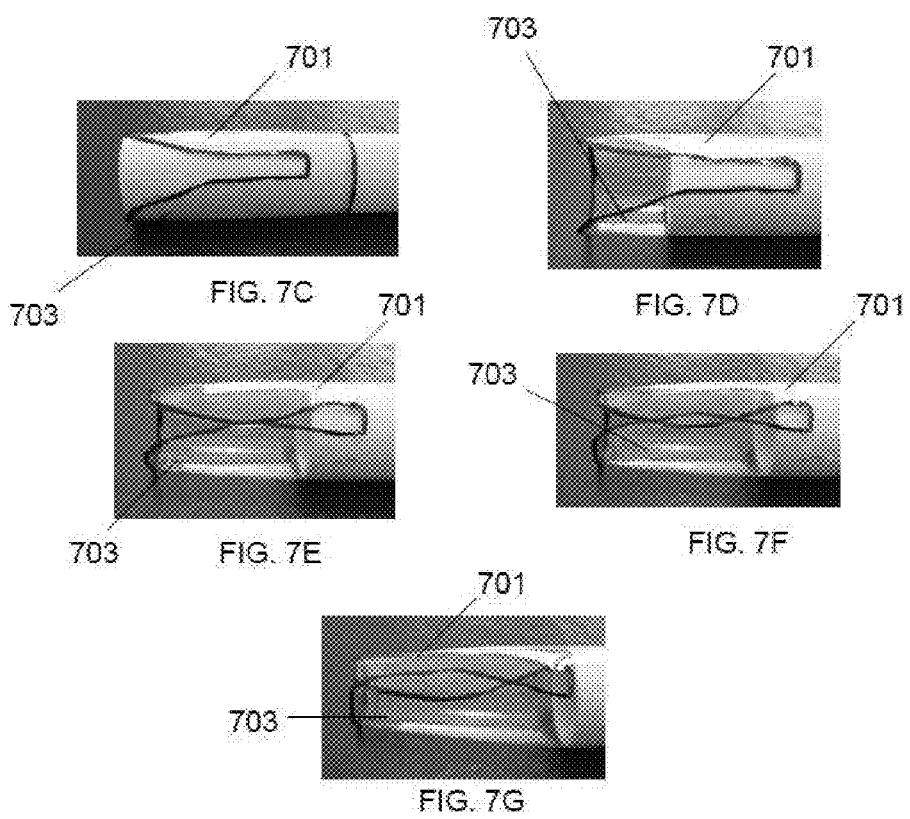

SYSTEMS AND METHODS FOR REMOVAL OF INTRAVASCULAR LEADS

RELATED APPLICATIONS

This application claims priority to and benefits of U.S. Provisional Application No. 61/296,610, filed Jan. 20, 2010, U.S. Provisional Application No. 61/305,824, filed Feb. 18, 2010, U.S. Provisional Application No. 61/314,883, filed Mar. 17, 2010, U.S. Provisional Application No. 61/332,007, filed May 6, 2010, U.S. Provisional Application No. 61/362,070, filed Jul. 7, 2010, U.S. Provisional Application No. 61/368,898, filed Jul. 29, 2010, and U.S. Provisional Application No. 61/420,008, filed Dec. 6, 2010. The entirety of all of these applications are hereby incorporated herein by reference for the teachings therein.

TECHNICAL FIELD

The presently disclosed embodiments relate to systems and methods for removal of implanted articles, and more particularly to systems and methods for removal of intravascular leads from blood vessels.

BACKGROUND

Implantable pacemakers and automatic implantable defibrillators contain intravascular leads that are typically inserted into a blood vessel of a patient, for instance, the internal jugular or subclavian vein. Such a lead can be advanced into the heart, where the distal section of the lead can be attached to the endocardial surface. Over time, however, the lead may fracture and become non-functional, so that a new lead may need to be inserted to replace the existing lead. The inoperative lead may also need to be removed from the vascular system, overtime, as it may get infected and may increase likelihood of blood clot formation. Removal of an inoperative lead, however, is oftentimes difficult because such a lead may have become ingrown within the vascular system, where fibrous adhesions may have formed between the lead and blood vessels.

Inoperative lead, in general, may sometimes be removed by simply pulling the free end of the lead to separate the lead from fibrous adhesions. However, this may lead to the creation of emboli in the blood stream by dislodging the fibrous adhesions in whole or in part, and may result in severe complication or even death of the patient. Several systems have been proposed for removal of inoperative leads. For example, U.S. Pat. No. 4,582,056 to McCorkle, Jr. et al. discloses a system that places a locking stylet inside the lead, enabling the physician to place traction on the lead. Sheaths of increasing diameter may then be advanced over the lead and rotated to disrupt the adhesions and allow lead removal. Because most leads have a substantially soft body, when an extraction sheath is advanced, the lead will tend to buckle and bunch up in front of the distal cutting end of the sheath. The buckling lead can increase the potential for the extraction sheath to veer out of axial alignment with the vein, and cut through the wall of the vein during advancement. This potential of the lead to bunch up and veer out of axial alignment can be increased in more recent extraction systems, because the more recent systems also include laser or radiofrequency cutting energy in addition to an extraction sheath.

Accordingly, there is a need for improved systems and methods for extraction of implanted articles, that can easily extract intravascular leads without some of the issues noted.

SUMMARY OF THE INVENTION

According to aspects illustrated herein, there is provided a system for extraction of an implanted article that includes an elongated member and a guide member disposed at a distal section of the elongated member. The guide member may define a pathway through which an implanted article can be securely received. The device can further include a dissection mechanism, coupled to the elongated member and designed to be positioned about the implanted article, for dissecting a fibrous adhesion about the implanted article.

According to aspects illustrated herein, there is also provided a system for extraction of an implanted article that includes a guide member. The guide member may define a pathway configured to accommodate an implanted article therethrough The device further includes a dissection mechanism, in communication with the guide member and designed to accept the implanted article accommodated in the pathway, for dissection of a fibrous adhesion around the implanted article.

According to aspects illustrated herein, there is provided further a method for extraction of an implanted article. To extract an implanted article, a proximal end of the implanted article may be accommodated in a pathway defined by a guide member. Next, a dissection mechanism may be positioned about the implanted article so as to enable the dissection mechanism to dissect a fibrous adhesion about the implanted article accommodated in the pathway. Subsequently, the guide member and the dissection mechanism may be advanced along the implanted article to a site of the fibrous adhesion to dissect the fibrous adhesion.

BRIEF DESCRIPTION OF THE DRAWINGS

FIGS. 7A-7G illustrate yet another embodiment of a dissection mechanism of an extraction system of the present disclosure.

DESCRIPTION OF SPECIFIC EMBODIMENTS

An extraction system 100 for removal of an implanted article, such a pacemaker lead, from, for instance, a vessel, is shown generally in FIG. 1. The extraction system 100 may be employed to dissect a fibrous adhesion connecting an implanted article to a vessel for subsequent removal of the implanted article from the vessel. The extraction system 100 includes, in one embodiment, an elongated member 102 having a proximal section 103, a distal section 104, and a longitudinal axis A extending the length of the elongated member 102. The elongated member 102, if desired, can be of any length sufficient for the elongated member 102 to be advanced along an implanted article. In an embodiment, the length of the elongated member 102 may range from about 40 cm to about 70 cm, although shorter or longer lengths may also be possible. In addition, the elongated member 102 may have an outer diameter ranging from about 2 F to about 7 F in size.

The elongated member 102, in accordance with an embodiment of the present disclosure, may be designed to navigate along a guide wire, a guide catheter, or both to a site of fibrous adhesion about an implanted article. To that end, the member 102 may be sufficiently rigid axially along its length, while remaining sufficiently flexible radially from side to side. To provide the elongated member with such characteristic, in an embodiment, the elongated member 102 may be made from a plastic or metallic material or a combination thereof. If desired, the elongated member 102 may be made from a sufficiently inelastic material to provide the elongated member 102 with additional radial rigidity. In an embodiment, the elongated member 102 may also be made from a biocompatible material. The elongated member 102 may additionally include a material that can minimize or reduce friction, so as to facilitate advancement of the elongated member 102 to a site of fibrous adhesion about the implanted article. To further minimize friction, alternatively or additionally, the elongated member may be coated with a hydrophilic coating, such as, for example, polyvinylpyrrolidone, polyurethane, poly(acrylic acid), poly(methacrylic acid), poly(dimeth)acrylamide, PTFE, poly(acrylamide), polyvinybutyrol, poly(hydroxyethylmethacrylate) or combinations thereof. The elongated member 102 may also be coated with an anti-thrombogenic coating, such as heparin (or its derivatives), urokinase, or PPack (dextrophenylalanine proline arginine chloromethylketone) to prevent thrombosis or any other adverse reaction due to the introduction of the elongated member 102 into the body of a patient. Other components of the extraction system 100, as will be described below, may also be coated with a hydrophilic coating, a anti-thrombogenic coating, or both.

Figure 2:
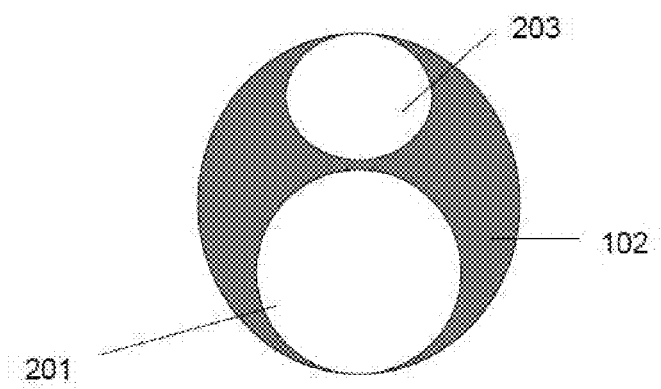
FIG. 2 is a cross sectional view of an elongated member of an extraction system of the present disclosure.

In an embodiment, the elongated member 102 may include one or more inner lumens 201, 203 for passing materials or instrumentation therethrough, as illustrated in FIG. 2. The inner lumens 201, 203 may include a coating layer, as described above, to minimize or reduce friction as the materials or instrumentation are passed through the lumens. At least one lumen of the elongated member 102 may be dimensioned to accept a guide wire, a guide catheter, or both to enable the elongated member 102 to navigate to a site of fibrous adhesion about the implanted article.

Figure 1A:
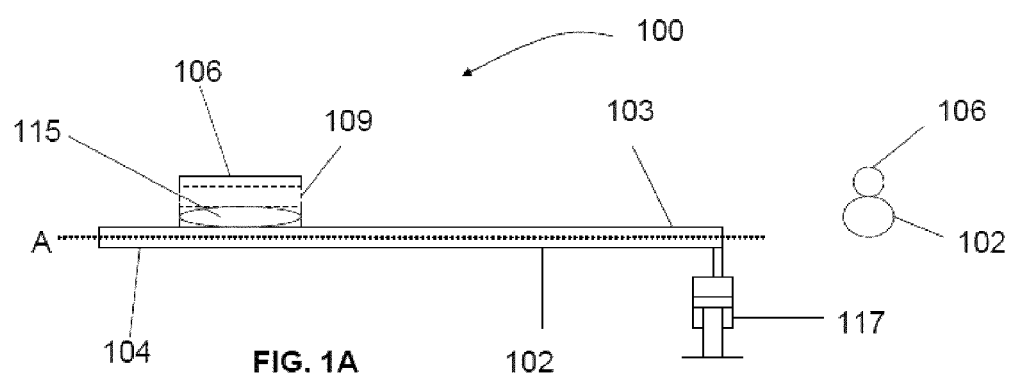
FIGS. 1A-1B are schematic views of embodiments of an extraction system of the present disclosure.
Figure 1B:
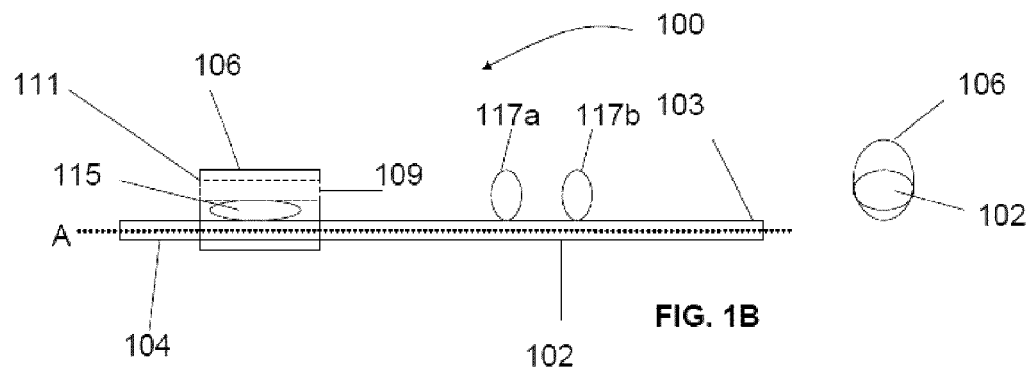
Figure 9A:
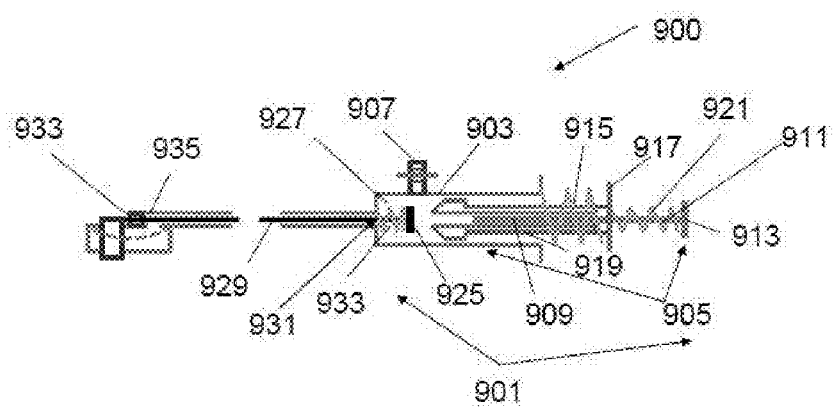
FIGS. 9A-9D are schematic views of an actuating mechanism of an extraction system of the present disclosure.

The extraction system 100 can further include a guide member 106 positioned at the distal section 104 of the elongated member 102. The guide member 106 may, in an embodiment, be disposed on the surface of the elongated member 102, as illustrated in FIG. 1A. Alternatively, the guide member 106 may surround the elongated member 102, as illustrated in FIG. 1B. The guide member 106 may include, in various embodiments, one or more tubes of various lengths or, for instance, any other design capable of accommodating the implanted article. For example, open or closed loops or rings, such as illustrated in FIG. 9A, can be used. In another embodiment, the guide member 106 may have a length sufficient to accommodate substantially the entire length of the implanted article. By providing the guide member 106 with such a length, the implanted article may remain within the guide member 106 following separation of the implanted article from the surrounding tissue to minimize further contact between the implanted article and the surrounding tissue, and can aid in the ease of the removal of the implanted article from the body of the patient. The guide member 106, in an embodiment, may be provided with an external diameter that permits the guide member to be advanced through a vessel, such as a blood vessel. It should be appreciated that while the extraction system 100 may be described and illustrated as having a single guide member 106, the extraction system 100 may include multiple guide members 106. Moreover, although the guide member 106 is described and illustrated herein as a separate element, it should be appreciated that, in certain embodiments, one or more inner lumens of the elongated member 102 may serve as the guide member 106.

As illustrated in FIGS. 1A-1B, the guide member 106 can define a pathway 109 through which an implanted article can pass and be accommodated. In an embodiment, the pathway 109 may be substantially parallel to the longitudinal axis A of the elongated member 102. In another embodiment, the pathway 109 may be configured to position the implanted article received in the pathway 109 substantially parallel to longitudinal axis A of the elongated member 102. The pathway 109 may, in an embodiment, have a length similar to that of the guide member 106. In other embodiments, the pathway 109 may extend beyond the guide member 106, and maybe in axial alignment therewith.

The pathway 109, in an embodiment, can be configured to substantially secure the implanted article within the pathway 109. In this way, when a fibrous adhesion around the implanted article is severed, the implanted article can remain securely positioned within the pathway 109. The pathway 109, in one embodiment, may be of any length, as long as the implanted article being accommodated in the pathway 109 can receive sufficient support. In an example, the length of the pathway 109 may range from about 0.25 cm to about 3 cm, although shorter or longer lengths may also be possible. Moreover, the pathway 109 may be sized so that the pathway 109 forms a substantially snug fit over the implanted article, while still allowing the guide member 106 to move over and about the implanted article. In an embodiment, the pathway 109 may be provided with any size and shape that may enable the pathway 109 to securely receive and accommodate an implanted article. Accordingly, the size and shape of the pathway 109, may vary depending on the requirements of a particular procedure, that is, depending on the shape and size (i.e., diameter) of the implanted article to be extracted. By way of a non-limiting example, the pathway 109 may have a diameter ranging from between about 2 F and about 10 F (between about 1 mm and 3.5 mm). To the extent desired, the pathway 109 may be provided with a size and shape that compliment the size and shape of the guide member 106. Alternatively, the pathway 109 may be of a different size and shape in comparison to the guide member 106.

The guide member 106, as shown in FIGS. 1A-B, can also include a leading edge 111 and a trailing edge 113. In an embodiment, the leading edge 111 of the guide member 106 may be sharpened and/or tapered to enhance separation of the fibrous adhesion from the implanted article. It should be appreciated that any design known in the art for providing a sharpened and/or tapered edge may be employed in connection with the leading edge 111 of the guide member 106.

The guide member 106 may further include, in an embodiment, a securing mechanism 115 disposed in the pathway 109 of the guide member 106, as illustrated in FIGS. 1A-1B. The securing mechanism 115 may be designed to secure the implanted article within pathway 109, when a fibrous adhesion around an implanted article is dissected by, for example, the dissection mechanism 108. Such securing of the implanted article can decrease the likelihood of the dissection mechanism 108 deviating from the fibrous adhesion and injuring a healthy tissue adjacent to the implanted article. The securing mechanism 115, in one embodiment, may be a balloon, inflatable sleeve or cuff, or any adjustable mechanisms capable of securing the implanted article within the guide member 106. In such an embodiment, the securing mechanism 115 may be designed so that positive pressure can be introduced and maintained within the securing mechanism 115 to allow the securing mechanism 115 to be inflated, as desired.

Figure 3A:
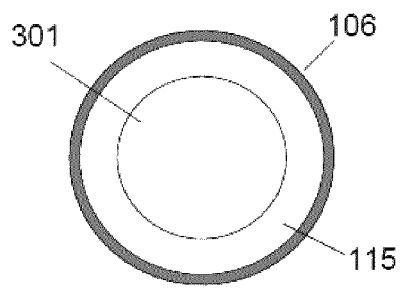
FIGS. 3A-3C illustrate various embodiments of a securing mechanism of an extraction system of the present disclosure.
Figure 3B:
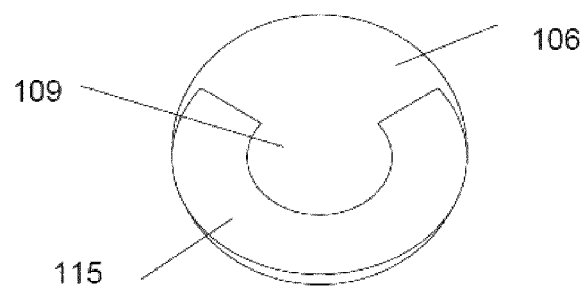
Figure 3C:
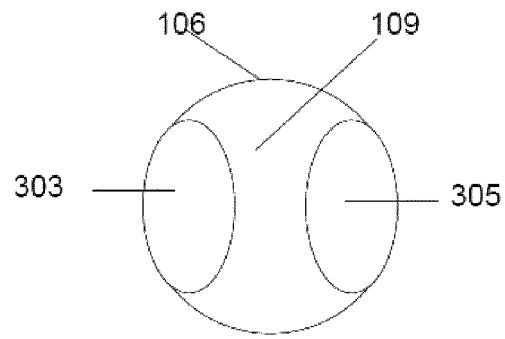

In one embodiment, the securing mechanism 115 can be designed to surround the implanted article, as illustrated in FIG. 3A. To that end, the securing mechanism 115 may have a toroidal shape with an inner opening 301, corresponding to the pathway 109, through which an implanted article can pass and be accommodated. In such embodiment, the securing mechanism 115 may also serve as a guide member or in place of the guide member 106. In another embodiment, as illustrated in FIG. 3B, the securing mechanism 115 may be situated at one side of the guide member 106, such that upon inflation, the securing mechanism 115 can act to push and secure the implanted article against the wall of the guide member 106. In yet another embodiments, as illustrated in FIG. 3C, the securing mechanism 115 can include multiple inflatable members 303, 305, such that upon inflation of the securing mechanism 115, the implanted article is secured between the multiple inflatable members 303, 305.

Referring now to FIG. 1B, in another embodiment, the extraction system 100 may include one or more loops 117a, 117a. The loops 117a, 117b may be employed, additionally or alternatively, to the securing mechanism 115, to secure the implanted article in place as the dissection mechanism 108 severs a fibrous adhesion around the implanted article. The loops 117a, 117b may have an inner diameter that can be releasably adjusted, when the implanted article extends therethrough, to secure the implanted article in place.

The extraction system 100 can further include a dissection mechanism 108. The dissection mechanism 108, in an embodiment, may be in communication with the guide member 106. In other words, the dissection mechanism 108 may be positioned such that the dissection mechanism 108 may dissect a fibrous adhesion around the implanted article accommodated in the guide member 106. The term "to dissect" as used herein means to separate at least a portion of a fibrous adhesion around the implanted article from a vessel in order to substantially eliminate a connective bond between the implanted article and the vessel. The separating of the fibrous adhesion from the vessel may be achieved by any mechanical means, such as, without limitation, by cutting, severing, stripping, splitting, or breaking up the adhesion from the vessel. Accordingly, the terms "cutting," "severing," "stripping," "splitting," and "breaking up" can be used interchangeably with the term "dissect" and with one another.

In some embodiments, the dissection mechanism 108 may be stationary with respect to the guide member 106. In other embodiments, the dissection mechanism 108 may be designed to translate with respect to the elongated member 102 or the guide member 106 from a first retracted position to a second advanced position. In an embodiment, the dissection mechanism 108 may translate substantially along the longitudinal axis A of the elongated member 102. To the extent necessary, the dissection mechanism 108 may be designed to be of any size, length, height, thickness, or geometric shape. Suitable dissection mechanisms include, but are not limited to, a blade, sheath, electrocautery, electrical wire, cutting electrode, any other mechanism capable of dissecting fibrous tissue.

In an embodiment, the dissection mechanism 108 may include both a mechanical element for mechanical dissection of a fibrous adhesion from a wall of a vessel, and a heating element (not shown), such as electrical wire or a radio frequency electrode, for heating the mechanical element to enhance the dissection of the fibrous adhesion from the wall of the vessel. In such an embodiment, the mechanical element may be formed from a material, such as ceramic, dielectric or any other material that can maintain heat and does not substantially conduct electricity. The heating element, in an embodiment, may be situated at the distal end of the mechanical element. The heating element may also be, in an embodiment, battery operated. The heating element, as desired, may act to heat the mechanical element to a sufficient temperature to sever tissue about the implanted article, while minimizing or reducing harm to the vessel wall. In some embodiments, the heating element may begin heating the mechanical element when the dissection mechanism 108 begins translating from the first retracted position toward the second advanced position. In other embodiments, the heating element may maintain the dissection mechanism 108 at an elevated temperature throughout the procedure. Should it be desired, the heating element may also act to heat the guide member 106 to enhance the dissection of the fibrous adhesion from the wall of the vessel.

In an embodiment, the dissection mechanism 108 may comprise a dissection sheath 501, as illustrated in FIGS. 4A-4B and 5A-5B. In an embodiment, the dissection sheath 501 may be provided with an inner diameter approximating the outer diameter of the implanted article during dissection. To that end, the dissection sheath 501 may act to dissect a fibrous adhesion in substantial proximity to an outer surface of the implanted article. In an embodiment, the dissection sheath 501 may include a sharpened or tapered leading rim 505 to facilitate in dissection of a fibrous adhesions. The dissection sheath 501 may also include, in one embodiment, a heating element 502. The heating element 503 may be embedded near the leading rim 505 of the dissection sheath 501 to heat the leading rim 505 in order to enhance severing of the fibrous adhesion from the wall of the vessel by the leading rim 505.

In order to cut the fibrous adhesion, the dissection sheath 501 may, in some embodiments, translate with respect to the elongated member 102 from a first retracted position to a second advanced position along the direction of longitudinal axis A. In an embodiment, the travel distance of the dissection sheath 501 can travel may be limited to reduce the likelihood that the dissection sheath 501 may deviate from the implanted article and/or a fibrous adhesion, causing injury to healthy tissue. In one embodiment, the travel distance of the dissection sheath 501 may be limited to a distance of approximately equal to about two to four times the diameter of the implanted article. As an example, such a distance may be about 5 to about 10 mm. Alternatively or additionally, the dissection sheath 501 may be rotatable to aid in the dissection of the fibrous adhesion.

Figure 4A:
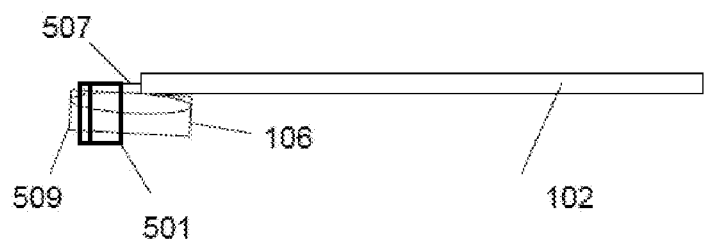
FIG. 4A-4B illustrate an embodiment of a dissection mechanism of an extraction system of the present disclosure.
Figure 4B:
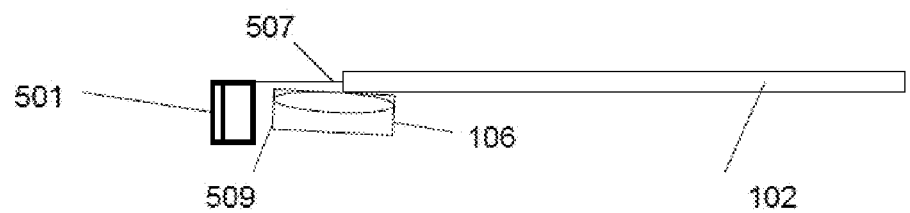
Figure 5A:
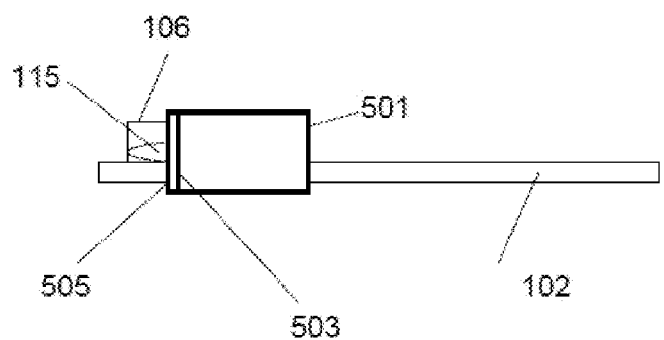
FIGS. 5A-5B illustrate another embodiment of a dissection mechanism of an extraction system of the present disclosure.
Figure 5B:
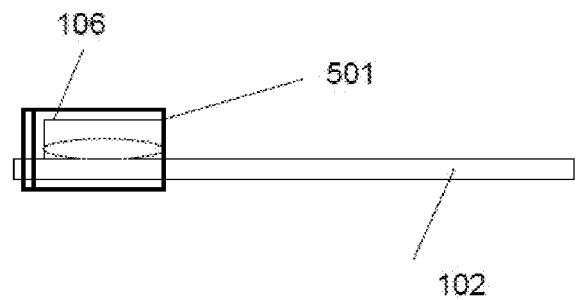

The dissection sheath 501 may, in various embodiments, be positioned about the elongated member 102, the guide member 106, or both. In one embodiment, as illustrated in FIGS. 4A-4B, the dissection sheath 501 may be situated circumferentially about the guide member 106 only. For example, the dissection sheath 501 may be concentric with the guide member 106. To position the dissection sheet 501 about guide member 106 only, a push rod 507 extending through the elongated member 102 may be provided to permit placement of the dissection sheath 501 distally of the elongated member 102. In such an embodiment, the dissection sheet 501 may be placed around a distal portion 509 of the guide member 106, which may extend distally of the distal portion 104 of the elongated member 102. The dissection sheet 501 can, in an embodiment, translate between a first retracted position, as illustrated in FIG. 4A, and a second advanced position, as illustrated in FIG. 4B. The dissection sheath 501 can translate between the first retracted position and the second advanced position by translation of the push rod 507. Alternatively, the dissection sheath 501 may be situated circumferentially about both the guide member 106 and the elongated member 102, as shown in FIGS. 5A-5B. Similarly to the embodiment shown in FIGS. 4A-4B, the dissection sheath 501 situated circumferentially about both the guide member 106 and the elongated member 102 can translate between the first advanced position, as shown in FIG. 5A, to the second advanced position, as shown in FIG. 5B.

Figure 6A:
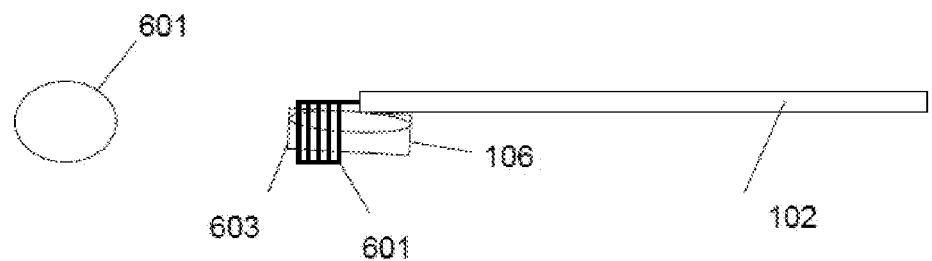
FIGS. 6A-6B illustrate yet another embodiment of a dissection mechanism of an extraction system of the present disclosure.
Figure 6B:
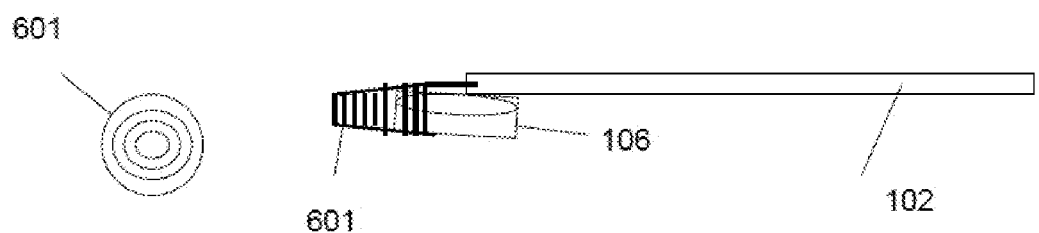

With reference to FIGS. 6A-6B, another embodiment of a dissection sheath is provided. As illustrated, dissection sheet 600 may include a spring 601, formed from, for instance, a wire, as shown in FIGS. 6A-6B. The spring 601 may be situated circumferentially about the guide member 106, so when the spring 601 is advanced, the spring 601 can dissect a fibrous adhesion around the implanted article accommodated in the guide member 106 from a vessel wall. In one embodiment, the spring 601 may be an overlapping spring, with an inner diameter approximating the outer diameter of the implanted article during dissection. By providing the spring 601 with such an inner diameter, the spring 601 may be able to dissect a fibrous adhesion in substantial proximity to an outer surface of the implanted article. The spring 601, in an embodiment, may also include a substantially sharpened or tapered leading edge 603 to facilitate in dissection of a fibrous adhesion. Additionally or alternatively, the spring 601 may be connected to a heating element in order to enhance dissection of the fibrous adhesion. The spring 601 may, in some embodiments, translate with respect to the elongated member 102 from a first retracted position to a second advanced position. As described above, the distance that the spring can translate from the distal end of the guide member 108 may be limited to reduce the likelihood that the spring 601 may be displaced from the implanted article and cause a perforation in the vessel. As the spring 601 is advanced distally, in an embodiment, the spring can be designed to rotate, creating a shearing action that can enhance severing of a fibrous adhesion between the implanted article and the vessel wall.

The spring 601 may, in an embodiment, be designed so that when in the first retracted position, the spring can be expanded into a tubular shape and can be situated about the guide member 108, as illustrated in FIG. 6A. The spring 601 may further be designed so that when deployed in the second advanced position, the spring 601 may form a trapezoid or conical shape, such as a funnel shape, as illustrated in FIG. 6B. In an embodiment, when the spring 601 forms a conical shape, the spring 601 may have an inner diameter in the narrowest section approximating the outer diameter of the implanted article.

Figure 7A:
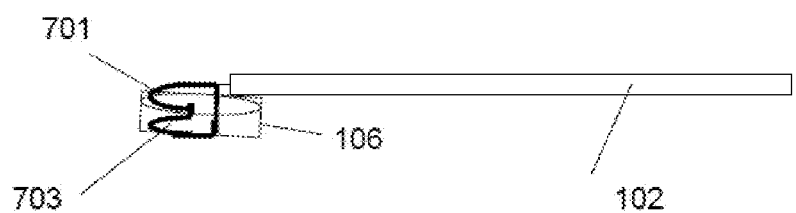
Figure 7B:
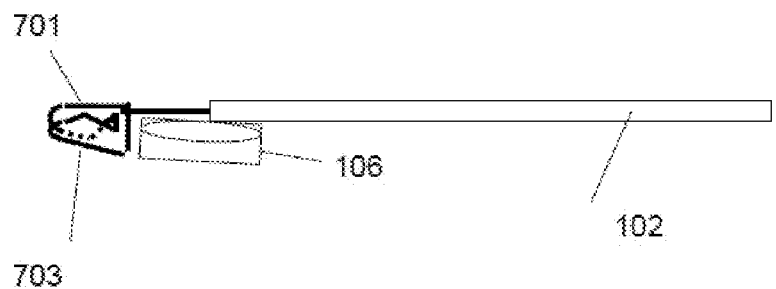

FIGS. 7A-7B illustrate yet another embodiment of the dissection mechanism 108. As shown in FIG. 7A, the dissection sheath 700 may be formed by one or more opposing blades 701, 703. The blades 701, 703, in an embodiment, may also include a substantially sharpened or tapered leading edge to sever the fibrous adhesion. Additionally or alternatively, at least one of the blades 701, 703 may be connected to a heating element in order to enhance severing of the fibrous adhesion.

In an embodiment, the blades 701, 703 may be designed so that, when the blades 701, 703 are situated over the guide member 106 in the first retracted position, the blades 701, 703 can be expanded to provide the dissection mechanism 108 with a tubular shape. On the other hand, the blades 701, 703 may be designed so that, when the blades are advanced toward the second advanced position, the blades 701, 703 may move radially inward toward one another, as illustrated in FIG. 7B. As the dissection mechanism 108 is advanced further forward, blades 701, 703 can continue to move radially inward toward one another until the blades 701, 703 overlap so as to provide scissor-like action to dissect the fibrous adhesion from the vessel wall.

FIGS. 7C-7G show the dissection mechanism 700 in various configurations. FIG. 7C shows the blades 701, 703 in a neutral and retracted configuration being situated circumferentially about the guide member 106. FIG. 7D shows the blades 701, 703 as the blades 701, 703 begin to advance distally of the guide member 106. FIG. 7E shows the blades 701, 703 as they continue to advance in the distal direction and begin to converge, forming an apex. FIG. 7F shows the blades 701, 703 as the blades 701, 703 begin to overlap. Finally, FIG. 7G shows the blades 701, 703 in a substantially contracted position in which the blades 701, 703 can act to dissect a fibrous adhesion between the implanted article and a vessel wall.

Figure 8A:
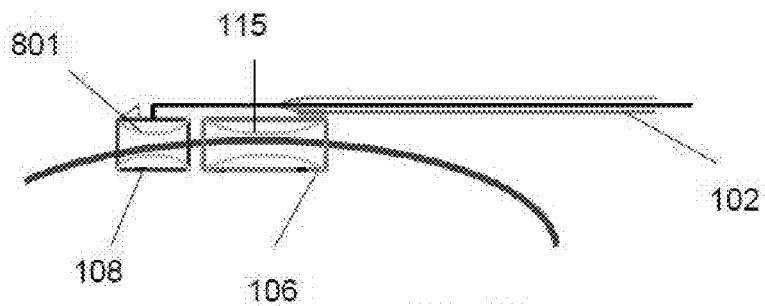
FIGS. 8A-8C are schematic views of an embodiment of an extraction system of the present disclosure.
Figure 8B:
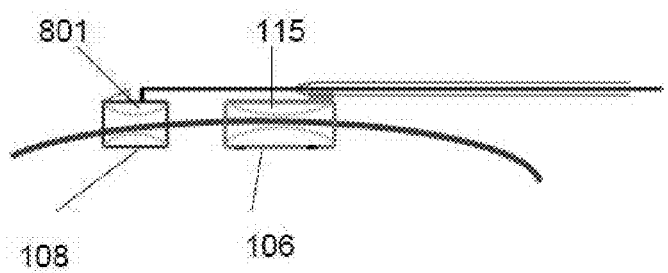
Figure 8C:
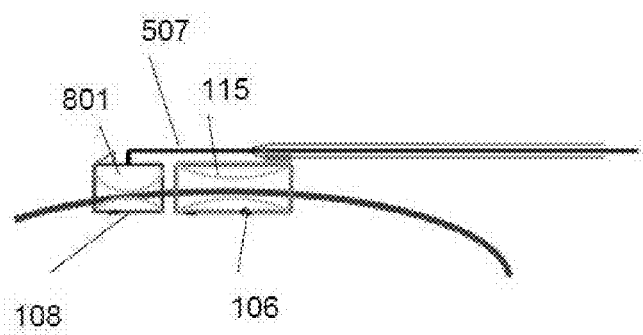

Looking now at FIGS. 8A-8C, in accordance with another embodiment of the present disclosure, the dissection mechanism 108 may be positioned distally of the guide member 106, instead of being positioned about the guide member 106. In such an embodiment, the implanted article may be accommodated through both the guide member 106 and the dissection mechanism 108. In an embodiment, the dissection mechanism 108 may be in substantial axial alignment with the guide member 106. As shown in FIGS. 8A-8C, the dissection mechanism 108, in an embodiment, may be provided with another securing mechanism 801, similar to the securing mechanism 115 disposed within the guide member 106. By providing the dissection mechanism 108 with the securing mechanism 801, the dissection mechanism 108 can be permitted to remain in place along the surface of the implanted article, without having to apply a substantially constant forward pressure to the extraction system 100.

Referring to FIGS. 9A-D, the extraction system 100 may further include an actuating mechanism 900. The actuating mechanism 900 may be employed to control inflation of the securing mechanism 115 inside the pathway 109, the securing mechanism 801 inside the dissection mechanism 108, or both. To the extent desired, the actuating mechanism 900 may be designed to also control the movement of dissection mechanism 108.

The actuating mechanism 900, in an embodiment, may include a pump 901 engaging the proximal end 103 of the elongated device 102. The pump 901 may be designed for advancing a fluid, liquid or gas, into the securing mechanism 115, the securing mechanism 801, or both to inflate one or both of these mechanisms. In an embodiment, the pump 901 may include a housing 903 designed to hold fluid to be deployed into the securing mechanism 115, the securing mechanism 801, or both. The housing 903 may also be designed to accommodate an activating mechanism 905 that may be used to move the fluid in or out of the housing 903. The pump 901 may further include, in an embodiment, a valve 907 through which a fluid may be delivered to or removed from the housing 903. In an embodiment, the valve 907 may be a Luer Lock adapter 3 way valve.

Still referring to FIG. 9A, the activating mechanism 900, in an embodiment, can include a first rod 909 engaged, at a proximal end 911, to a first pusher 913. The activating mechanism 900 may also include a piston 915 having a flange 917 at its proximal end 911, and a pathway 919 to accommodate the first rod 909. In an embodiment, the first rod 909 may be longitudinally moveable within the pathway 919 of the piston 915. A spring 921 can be situated about piston 915 between the flange 917 and proximal end 911, so as to return the piston 915 to its neutral position when no force is applied to the piston 915. The activating mechanism 900 can be sufficiently designed to push fluid from the housing 903 and into the securing mechanism 115, the securing mechanism 801, or both. In particular, the activating mechanism 900 may be designed so that, upon a single push of first pusher 913, the spring 921 may be depressed and the first rod 909 can be advanced forward so as to push fluid from the housing 901 and into the securing mechanism 115, the securing mechanism 801, or both to inflate the securing mechanism 115, the securing mechanism 801, or both. The first rod 909 may be returned to its original position to withdraw fluid from the securing mechanism 115, the securing mechanism 801, or both to deflate the securing mechanism 115, the securing mechanism 801, or both.

As illustrated in FIG. 9A, the actuating mechanism 900, in an embodiment, can further include a second pusher 925 situated at the distal end 927 of the housing 903. The second pusher 925 may include a second rod 929 designed to extend from a distal end 927 of the housing 901, through an opening 931 in the housing 901, and into one or more inner lumens of the elongated device 102. In an embodiment, the second rod 929 may be connected with the push rod 507. The second rod 929, in an embodiment, may be spring loaded by a spring 933 between the second pusher 925 and the distal end 927 of the housing 901 to permit the second pusher 925 to return to its neutral state when no force is applied thereto. The second rod 929 may be longitudinally moveable within one or more inner lumens of the elongated device 102 and can be designed to engage the dissection mechanism 108. When the activating mechanism 900 is activated, the first rod 909 is designed to push the second pusher 925 which is designed to move the second rod 929 through one or more of the elongated device 102, causing the dissection mechanism 108 to advance forward.

In one embodiment, the activating mechanism 900 may further include a seal 933 at or near a distal tip 935 of the second rod 929. The seal 933 may be designed to create a substantially fluid tight seal around the second rod 929 to minimize or prevent leakage of fluid from the securing members. Moreover, the seal 933 may further be designed to allow rod 1328 to be axially aligned within the on or more inner lumens of the elongated member 102.

In an embodiment, the actuating mechanism 900 may be designed so that following a single push of the first pusher 913, the actuating mechanism 900 may be released by removing pressure from first pusher 913. As shown in FIG. 9D, release of the first pusher 913, in an embodiment, may result in deflation of the securing mechanisms and/or retraction of the dissection mechanism 108. It should be noted that the springs may be designed to help return first pusher 913 and second pusher 925 to their original or starting positions.

Figure 10:
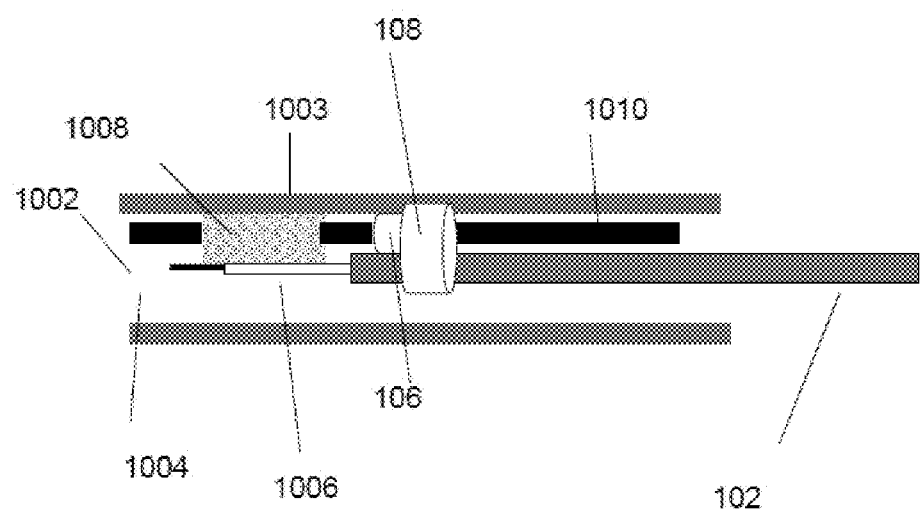
FIG. 10 shows an embodiment of an extraction system of the present disclosure in operation

In operation, the extraction system 100 may be utilized to dissect a fibrous adhesion from an implanted article, such as a pacemaker lead, so as to enable removal of the implanted article. In an embodiment, as illustrated in FIG. 10, a fibrous adhesion 1008 may exist between an implanted article 1010 and a vessel 1002, such as a blood vessel, adhering the implanted article 1010 to the vessel 1002. To gain access to the vessel 1002 to perform the extraction protocol, in an embodiment, a needle may first be used to provide an opening in the vessel 1002 through which a guide wire 1004, a guide catheter 1006 or both may be inserted to define a pathway for the elongated member 108 to navigate the site of fibrous adhesion 1008. The guide wire 1004, guide catheter 1006 or both may be designed to provide sufficient strength and rigidity to support the elongated member.

The elongated member 102 may then be directed over the guide wire, the guide catheter or both to the site of fibrous adhesion 1008. In an embodiment, before, or shortly after, the elongated member 102 enters the vessel 1002, the implanted article 1010 may be inserted into the guide member 106, so that the guide member 106 may be advanced distally until resistance is felt, signaling contact with fibrous adhesions.

Once the resistance is felt, the securing mechanism 115 may be inflated to maintain the guide member 106 in place. Next, the dissection mechanism 108 may be advanced distally to a preferred position to dissect the fibrous adhesion 1008 from the wall of the vessel 1002. Following dissection of the fibrous adhesion 1008, the securing mechanism 115 may be deactivated to release the implanted article 1010, so that the elongated member 102 can be advanced distally, if so desired.

In the embodiment with the securing mechanisms 115 in the pathway 109 and the securing mechanism 801 disposed in the dissection mechanism 108, both the securing mechanisms may be initially deflated, as shown in FIG. 8A. Then, the securing mechanism 115 may be inflated to maintain the implanted article in place, while keeping the securing mechanism 801 deflated. Next, the dissection mechanism 108 may be advanced distally to a preferred position to sever a fibrous adhesion, as shown in FIG. 8B. Once the fibrous adhesion is severed and the dissection mechanism 108 is in the preferred position, the securing mechanism 801 may be inflated to maintain the dissection mechanism 108 in place. Subsequently, the securing mechanism 115 may be deflated, so as to permit the advancement of the guide member 106 distally toward the dissection mechanism 108, as shown in FIG. 8C.

The elongated member 102 may then be advanced distally to a site of another adhesion between the implanted article 1010 and the vessel 1002 to sever that adhesion and to substantially eliminate another connective bond between the implanted article 1010 and the vessel 1002. This process may be repeated until all connective bonds between the implanted article 1010 and the vessel 1002 have been eliminated. Once all connective bonds between the implanted article 1010 and the vessel 1002 have been eliminated, the implanted article 1010 can be removed from the patient's body.

Figure 9B:
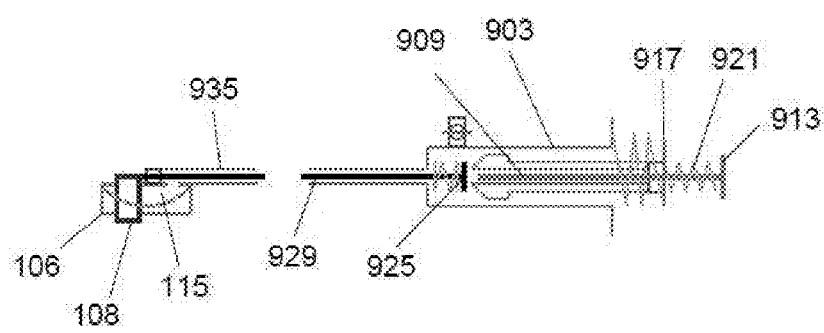
Figure 9C:
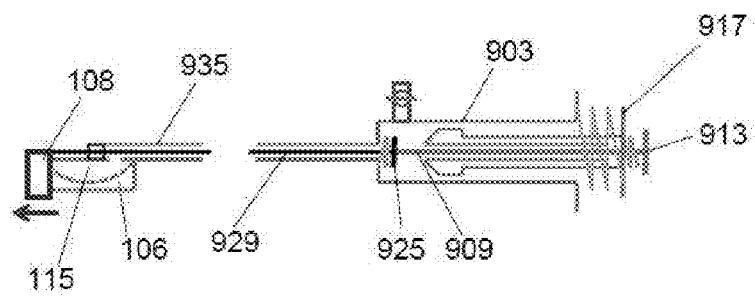
Figure 9D:
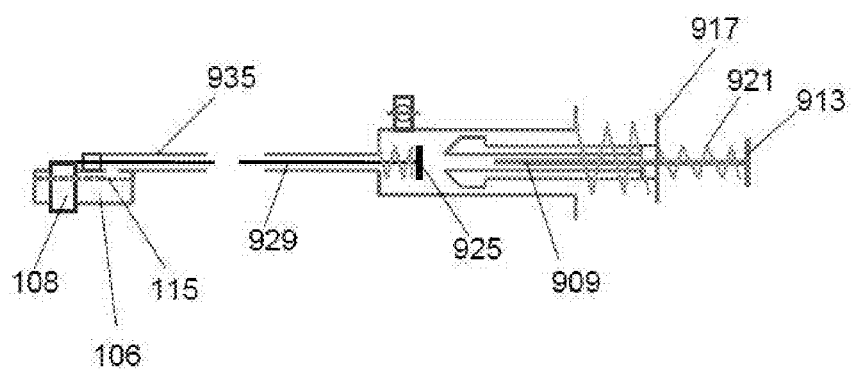

In reference to FIGS. 9B-9D, when using the actuating mechanism 900, once the guide member 106 is at a site of interest, the actuating mechanism 900 may be deployed. First, the first pusher 913 may be pushed to advance the first rod 909 in the distal direction, resulting in the inflation of the first securing mechanism 115 to secure the implanted article 1010 within the guide member 106, as shown in FIG. 9B. Once the first rod 909 reaches second pusher 925, the first rod 909 can act to push against the second pusher 925, causing the second rod 929 to advance forward. When the second rod 929 advances forward, the second rod 929 can cause the dissection mechanism 108 to move to the second advanced position to dissect the fibrous adhesion 1008 from the wall of the vessel 1002, as shown in FIG. 9C. Once the fibrous adhesion 1008 is dissected from the wall of the vessel 1002, the actuating mechanism 900 may be released by removing pressure from first pusher 909, causing retraction of the dissection mechanism 108 and deflation of the securing mechanism 115, as shown in FIG. 9D. Following release of the actuating mechanism 900, the extraction system may be advanced distally to a site of another adhesion.

Endoscopic visualization may also be added to the dissection process, to impart additional control. In one embodiment, an endoscope, such as a transparent conical tipped endoscope, may be passed through the elongated member 102 and advanced out of the elongated member 102 to visualize a fibrous adhesion as the fibrous adhesion is dissected. In another embodiment, an endoscope may be situated inside the dissection sheath 501. In such an embodiment, the dissection sheath 501 can telescope forward to dissect a fibrous adhesion, while the leading rim 505 of the dissection sheath 501 is visualized by the endoscope. Saline irrigation may be required to clear the area distal to the endoscope. Other imaging techniques for monitoring, x-ray, fluoroscopy, magnetic resonance imaging (MRI), ultrasound imaging, Fourier transform infrared spectroscopy, ultraviolet or visible spectroscopy, may be utilized to monitor the extraction of the implanted article.

Although described and illustrated in connection with removing a pacemaker lead from a blood vessel, the extraction system 100 of the present disclosure may also be utilized to remove implanted articles other than pacemaker leads. The extraction system 100 may also be utilized to remove implanted articles from locations other than the vascular system. Finally, it should be understood that the extraction system 100 may be employed for purposes other than removing implanted articles, such as, for example, harvesting tissue.

While the invention has been described in connection with the specific embodiments thereof, it will be understood that it is capable of further modification. Furthermore, this application is intended to cover any variations, uses, or adaptations of the invention, including such departures from the present disclosure as come within known or customary practice in the art to which the invention pertains, and as fall within the scope of the appended claims.

What is claimed is:
1. An extraction system comprising:
   an elongated member;
   a guide member disposed at a the distal section of the elongated member and having a pathway through which an implanted article can be securely received; and
   a dissection mechanism, coupled to the elongated member and designed to be positioned about the implanted article, the dissection mechanism including opposing blades that overlap when the dissection mechanism is in an advanced position so as to provide scissor-like action to dissect a fibrous adhesion about the implanted article.
2. The system of claim 1, wherein the dissection mechanism is designed to be translated from a first retracted position to a second advanced position.
3. The system of claim 1, wherein the dissection mechanism is concentric with the guide member.
4. The system of claim 1, wherein the dissection mechanism is situated circumferentially about the guide member and the elongated member.
5. The system of claim 1, wherein the dissection mechanism is in axial alignment with the guide member.
6. The system of claim 1 further comprising a first securing mechanism disposed in the pathway.
7. The system of claim 1 further including a second securing mechanism disposed within the dissection mechanism.
8. The system of claim 1 further including a heating element disposed within the dissection mechanism.
9. A device for extraction comprising:
   a guide member;
   a pathway, defined by the guide member and configured to accommodate an implanted article therethrough; and
   a dissection mechanism, in communication with the guide member and designed to accept the implanted article, the dissection mechanism including opposing blades that overlap when the dissection mechanism is in an advanced position so as to provide scissor-like action to dissect of a fibrous adhesion around the implanted article.
10. The device of claim 9, wherein the dissection mechanism is designed to translate from a first retracted position to a second advanced position.
11. The device of claim 9, wherein the dissection mechanism is concentric with the guide member.
12. The device of claim 9, wherein the dissection mechanism is in axial alignment with the guide member.
13. The device of claim 9 further including a second securing mechanism disposed in the pathway.
14. The device of claim 9 further including a second securing mechanism disposed within the dissection mechanism.

* * * * *